(12) United States Patent
Li et al.

(10) Patent No.: US 9,958,378 B2
(45) Date of Patent: May 1, 2018

(54) BODY FLUID TEST SYSTEM AND MOVING MECHANISM THEREOF

(71) Applicant: Wistron Corp., New Taipei (TW)

(72) Inventors: Chuan-Sheng Li, New Taipei (TW); Yu-Jung Chu, New Taipei (TW)

(73) Assignee: WISTRON CORP., New Taipei (TW)

( * ) Notice: Subject to any disclaimer, the term of this patent is extended or adjusted under 35 U.S.C. 154(b) by 85 days.

(21) Appl. No.: 15/158,019

(22) Filed: May 18, 2016

(65) Prior Publication Data
US 2017/0241900 A1    Aug. 24, 2017

(30) Foreign Application Priority Data
Feb. 19, 2016  (TW) .............................. 105104911 A

(51) Int. Cl.
| | | |
|---|---|---|
| *H01J 40/14* | (2006.01) | |
| *G01N 21/17* | (2006.01) | |
| *G01N 33/487* | (2006.01) | |
| *G01N 35/04* | (2006.01) | |
| *G01N 35/00* | (2006.01) | |
| *G01N 35/10* | (2006.01) | |

(52) U.S. Cl.
CPC ....... *G01N 21/17* (2013.01); *G01N 33/48778* (2013.01); *G01N 35/00029* (2013.01); *G01N 35/04* (2013.01); *G01N 35/1009* (2013.01)

(58) Field of Classification Search
CPC ... G01N 21/17; G01N 33/48778; G01N 35/04
USPC .................................. 250/221, 573; 422/73
See application file for complete search history.

(56) References Cited

U.S. PATENT DOCUMENTS

| | | | |
|---|---|---|---|
| 4,873,875 A * | 10/1989 | Cork .................... | G01N 15/042 250/577 |
| 2010/0060062 A1* | 3/2010 | Koga .................. | B60N 2/0232 297/344.1 |

\* cited by examiner

*Primary Examiner* — Kevin Pyo
(74) *Attorney, Agent, or Firm* — Nixon Peabody LLP

(57) ABSTRACT

A body fluid test system includes a test chip, an image capturing device, a moving mechanism for test tube and at least one fluid transfer device. The image capturing device is for capturing image of the test chip. The moving mechanism includes a base and a test tube carrier. The test tube carrier is movably disposed on the base. The test tube carrier is for carrying at least one test tube. One end of the fluid transfer device corresponds to the top of the test tube carrier, and another end of the fluid transfer device corresponds to the test chip. The test tube carrier is movable upwardly from a pre-testing position to a testing position. When the test tube carrier is at the testing position, the fluid transfer device is for transferring a body fluid sample contained in the at least one test tube to the test chip.

12 Claims, 5 Drawing Sheets

US 9,958,378 B2

BODY FLUID TEST SYSTEM AND MOVING MECHANISM THEREOF

CROSS-REFERENCE TO RELATED APPLICATIONS

This non-provisional application claims priority under 35 U.S.C. § 119(a) to Patent Application No(s). 105104911 filed in Taiwan, R.O.C. on Feb. 19, 2016, the entire contents of which are hereby incorporated by reference.

TECHNICAL FIELD

The disclosure relates to a moving mechanism and a body fluid test system, more particularly to a moving mechanism for test tube and a body fluid test system having the moving mechanism.

BACKGROUND

Some diseases such as tumors, chronic urticaria and lung diseases are able to be diagnosed by blood test. Before taking the blood test, a blood sample contained in a test tube is left and untouched for a particular period of time until the blood sample is in a stable state. Then, a medical worker will bring the test tube to a blood testing device, and use a syringe and a tube to draw the blood sample. The drawn blood sample is then transferred into a test chip. Then, a light source generates light incident on the test chip, and then a camera captures a cell image of the blood sample in the test chip for helping the medical worker to diagnose the diseases.

SUMMARY

The present disclosure provides a moving mechanism and a body fluid test system having the moving mechanism for solving the problem that the body fluid sample contained in the test tube is easily disturbed when the test tube is moved to the blood testing device.

One embodiment of the disclosure provides a body fluid test system including a test chip, an image capturing device, a moving mechanism for test tube and at least one fluid transfer device. The image capturing device is used for capturing image of the test chip. The moving mechanism includes a base and a test tube carrier. The test tube carrier is movably disposed on the base. The test tube carrier is used for carrying at least one test tube. One end of the fluid transfer device corresponds to the top of the test tube carrier, and another end of the fluid transfer device corresponds to the test chip. The test tube carrier is movable upwardly from a pre-testing position to a testing position. When the test tube carrier is at the testing position, the fluid transfer device is for transferring a body fluid sample contained in the at least one test tube to the test chip.

One embodiment of the disclosure provides a moving mechanism for test tube. The moving mechanism includes a base and a test tube carrier. The test tube carrier is movably disposed on the base. The test tube carrier is used for carrying at least one test tube. The test tube carrier is movable upwardly from a pre-testing position to a testing position.

BRIEF DESCRIPTION OF THE DRAWINGS

The present disclosure will become more fully understood from the detailed description given hereinbelow and the accompanying drawings which are given by way of illustration only and thus are not limitative of the present disclosure and wherein.

DETAILED DESCRIPTION

Figure 1:
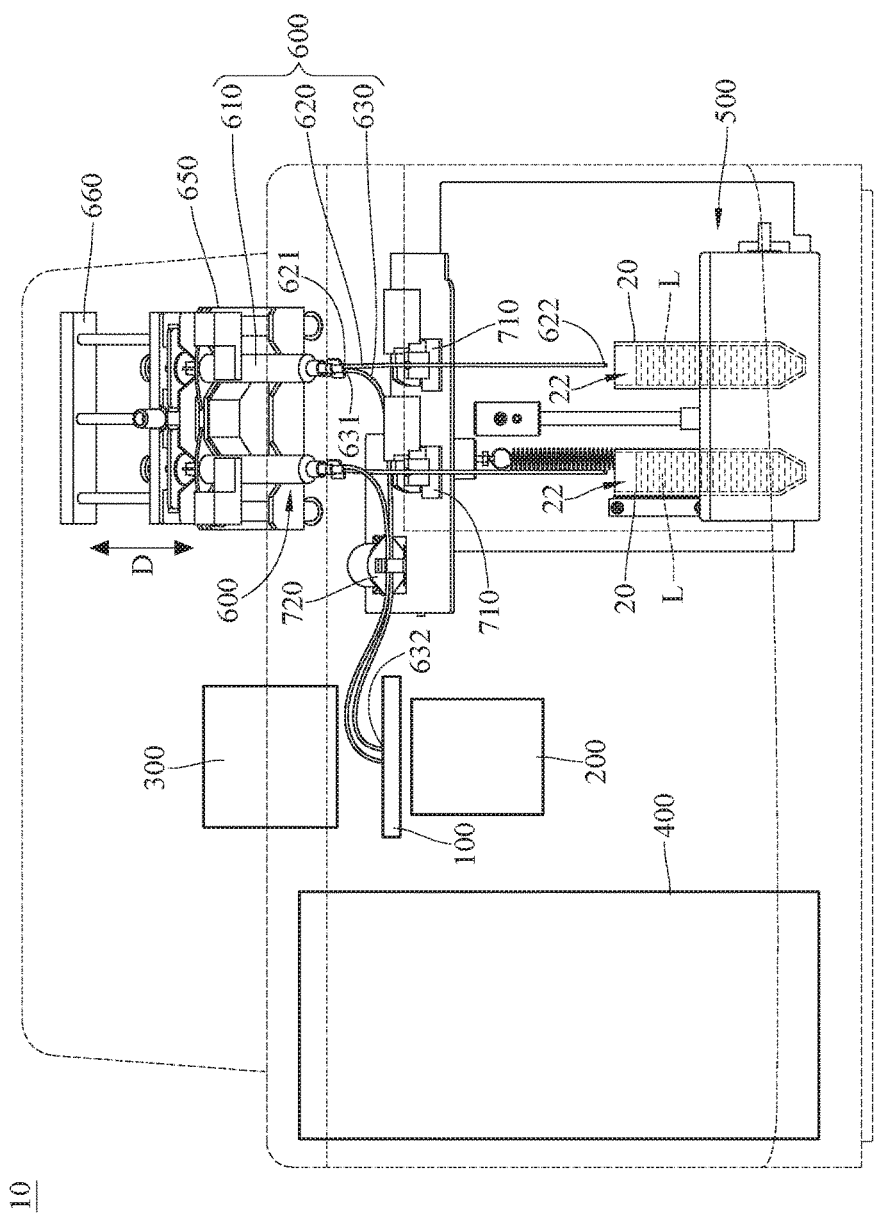
FIG. 1 is a schematic plan view of a body fluid test system according to a first embodiment of the disclosure.

In the following detailed description, for purposes of explanation, numerous specific details are set forth in order to provide a thorough understanding of the disclosed embodiments. It will be apparent, however, that one or more embodiments may be practiced without these specific details. In other instances, well-known structures and devices are schematically shown in order to simplify the drawing.

Figure 2:
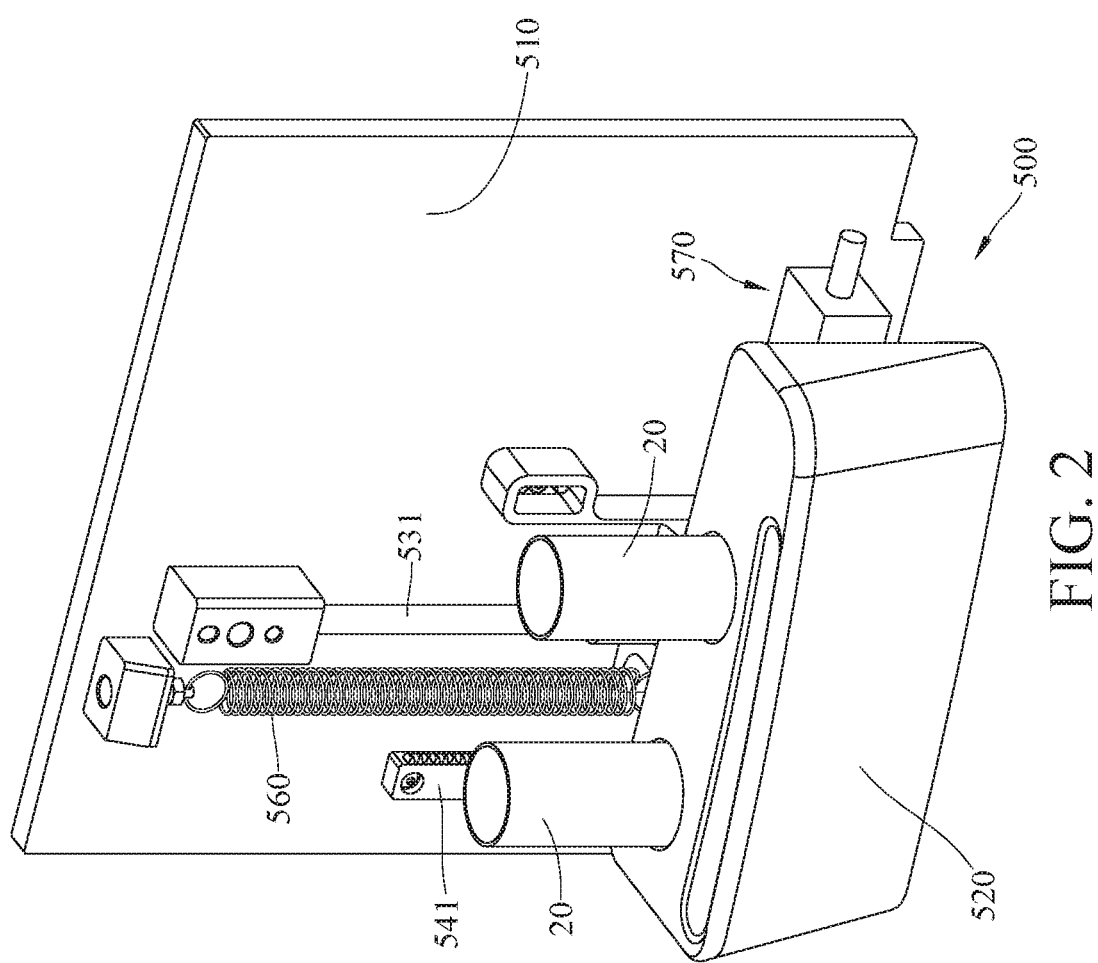
FIG. 2 is a perspective view of a moving mechanism in FIG. 1.
Figure 3:
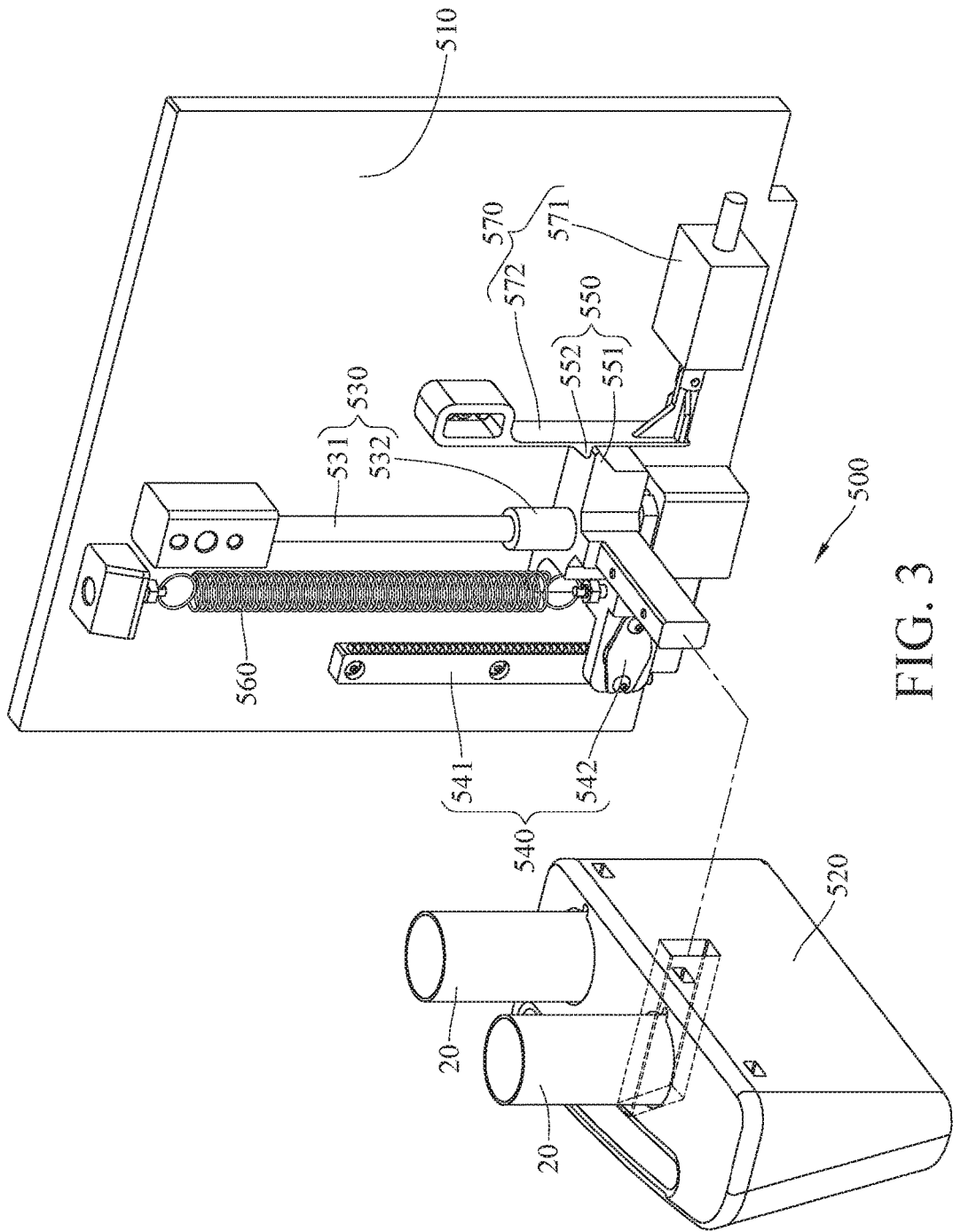
FIG. 3 is an exploded view of the moving mechanism in FIG. 2.

Please refer to FIG. 1 to FIG. 3, FIG. 1 is a schematic plan view of a body fluid test system according to a first embodiment of the disclosure, FIG. 2 is a perspective view of a moving mechanism in FIG. 1, and FIG. 3 is an exploded view of the moving mechanism in FIG. 2. As shown in FIG. 1, a body fluid test system 10 is provided. The body fluid test system 10 includes a test chip 100, an image capturing device 200, a light source 300, a fluid processing device 400, a moving mechanism 500 and two fluid transfer devices 600. The body fluid test system 10 is used for testing body fluid. For example, the body fluid test system 10 can detect the cancer cell or analyze the composition of the body flood sample.

In this embodiment, the test chip 100 has two channels (not shown in the drawings). Each of the two channels of the test chip 100 is provided for one type of body fluid sample to flow through. Thus, same type or two different types of body fluid samples are able to flow through the two channels of the test chip 100, respectively. However, the present disclosure is not limited to the configuration of the test chip 100 and the quantity of the channels in the test chip 100. In other embodiments, the quantity of the channels in the test chip can be one or over three. In addition, the body fluid sample is, for example, blood, saliva or urine.

The image capturing device 200 is, for example, a camera. The imaging capturing device 200 is used for capturing images of the body fluid sample in the channels of the test chip 100.

The light source 300 is, for example a light emitting diode (LED) or a Halogen Lamp. The light source 300 is used for generating light incident on the body fluid sample in the channels of the test chip 100. In this and other embodiments, the light generated by the light source 300 can be visible light or infrared light.

Figure 4:
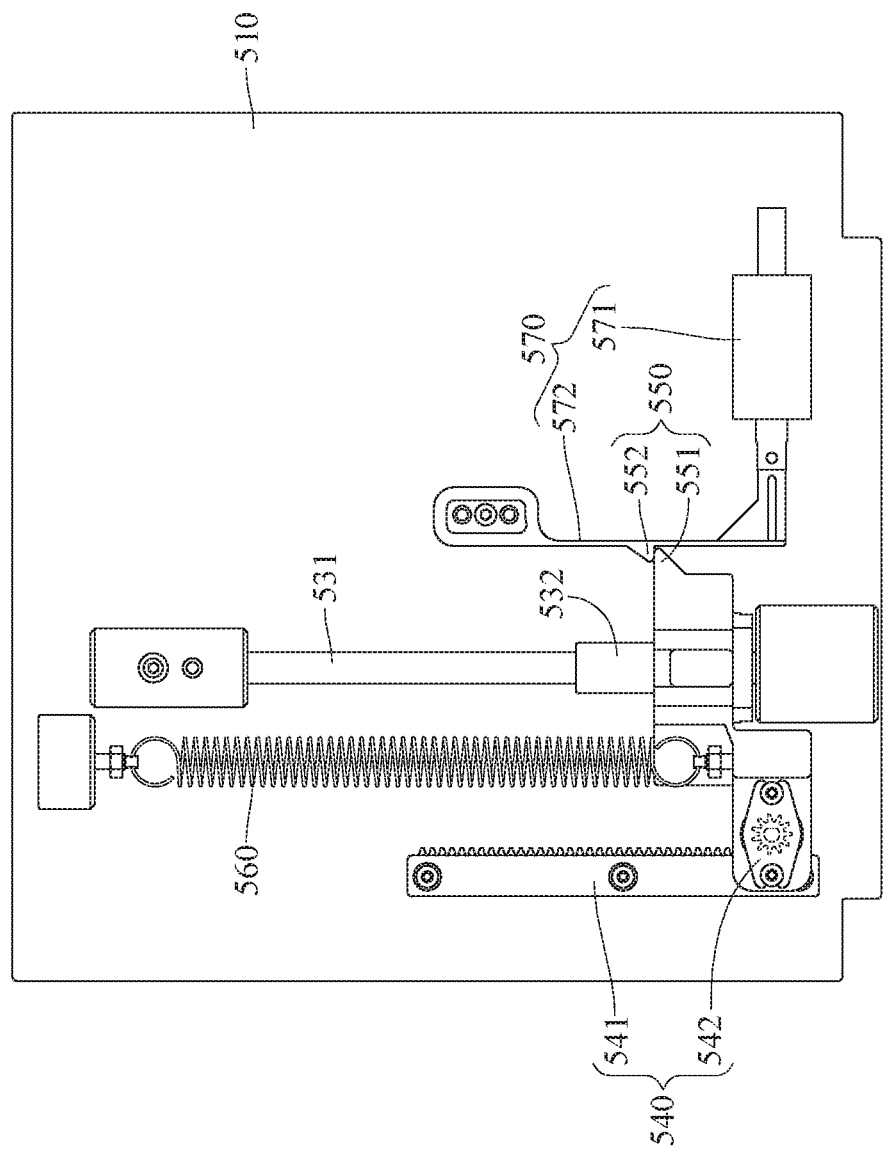
FIG. 4 is a schematic plan view of the moving mechanism in FIG. 2 when a test tube carrier is located at a pre-testing position.
Figure 5:
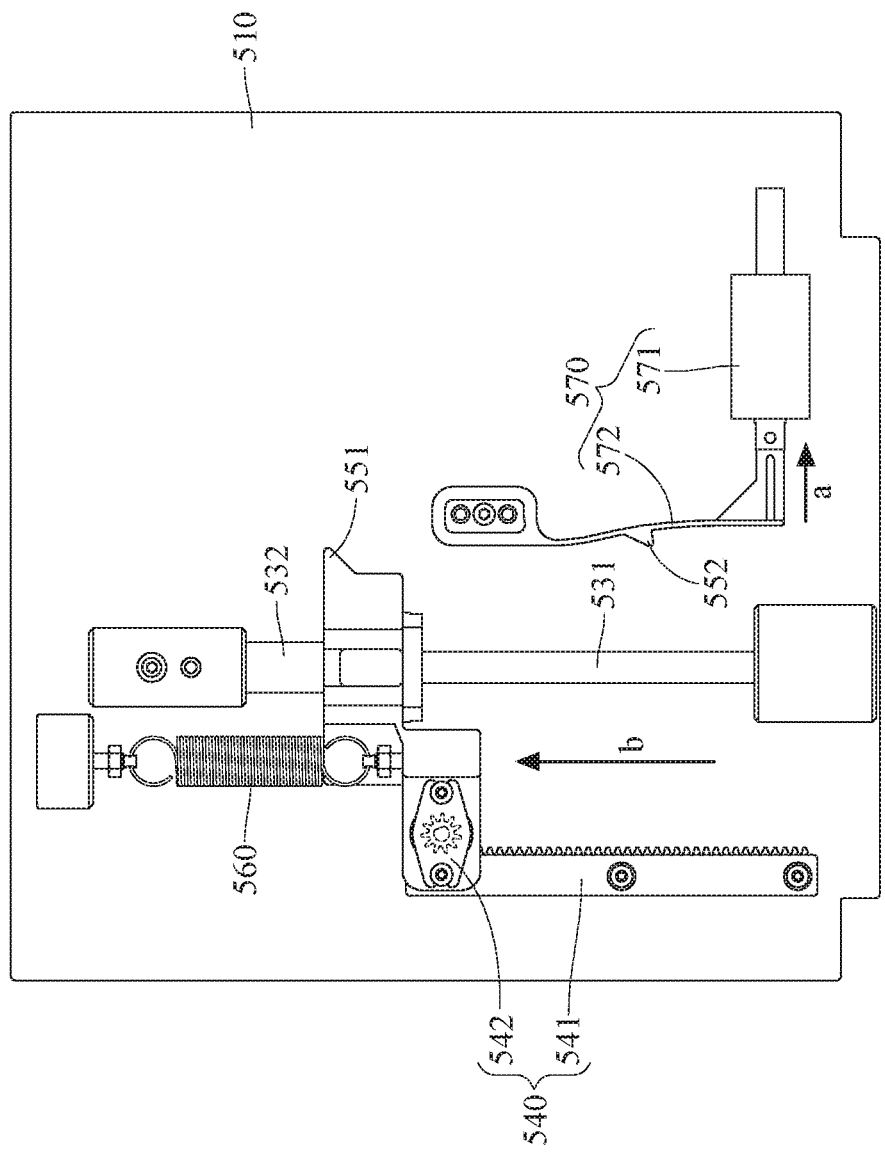
FIG. 5 is a schematic plan view of the moving mechanism in FIG. 2 when the test tube carrier is located at a testing position.

The fluid processing device 400 is used for processing the body fluid sample which has been tested. The moving mechanism 500 includes a base 510 and a test tube carrier 520. The test tube carrier 520 is movably disposed on the base 510. In this embodiment, the test tube carrier 520 is able to be moved between a pre-testing position (as shown in FIG. 4) and a testing position (as shown in FIG. 5). In detail, the test tube carrier 520 can be moved upwardly from the pre-testing position to the testing position and moved downwardly from the testing position to the pre-testing position. In this embodiment, the test tube carrier 520 is able to carry at least two test tubes 20. Each of the two test tubes 20 is able to contain the body fluid sample L. In addition, the quantity of the test tubes 20 is the same as the quantity of the channels in the test chip 100. Thus, the body fluid test system 10 is able to test multiple body fluid samples simultaneously.

Then, the connection between the base 510 and the test tube carrier 520 is described as follows. In detail, the moving mechanism 500 further includes a slide assembly 530, a decelerating assembly 540, a stop assembly 550 and an elastic member 560.

The slide assembly 530 includes a rail member 531 and a slidable member 532. The rail member 531 is disposed on the base 510 and extends along a surface of the base 510. The slidable member 532 is movably disposed on the rail member 531. The test tube carrier 520 is disposed on the slidable member 532. Thus, the test tube carrier 520 can be moved upwardly and downwardly relative to the base 510 when the slidable member 532 is moved upwardly and downwardly relative to the rail member 531.

The decelerating assembly 540 includes a gear rack 541 and a decelerating gear 542. The gear rack 541 is disposed on the base 510. The decelerating gear 542 is disposed on the test tube carrier 520 and engaged to the gear rack 541. The decelerating gear 542 is used for decelerating the speed of the test tube carrier 520. For example, the decelerating gear 542 allows the test tube carrier 520 to be moved upwardly and downwardly in a slow manner. In this embodiment, the decelerating gear 542 is, for example, a unidirectional damper. In addition, the present disclosure is not limited to the positions of the gear rack 541 and the decelerating gear 542. In other embodiments, the gear rack 541 can be disposed on the test tube carrier 520, and the decelerating gear 542 can be disposed on the base 510.

The stop assembly 550 includes a first stop block 551 and a second stop block 552. The first stop block 551 is disposed on the slidable member 532. The second stop block 552 is movably disposed on the base 510, so the second stop block 552 is able to press against the first stop block 551 for restricting the movement of the first stop block 551 or separate from the first stop block 551 for releasing the first stop block 551. In addition, the second stop block 552 is moved relative to the base 510 by a driving assembly 570. In detail, the driving assembly 570 includes a movable rod 571 and a flexible arm 572. The movable rod 571 is movably disposed on the base 510. One end of the flexible arm 572 is pivoted to the base 510, and another end of the flexible arm 572 is connected to the movable rod 571. The second stop block 552 is located on, for example, the middle part of the flexible arm 572.

When the movable rod 571 is moved relative to the base 510 to drive the flexible arm 572 to bend, an end of the flexible arm 572 connected to the movable rod 571 is moved away from the first stop block 551 so that the second stop block 552 on the flexible arm 572 is separated from the first stop block 551 for releasing the first stop block 551. In the reverse movement of the movable rod 571, the movable rod 571 is able to force the flexible arm 572 to drive the second stop block 552 to press against the first stop block 551 for restricting the movement of the first stop block 551.

The elastic member 560 is, for example, an extension spring. Two opposite ends of the elastic member 560 are respectively connected to the base 510 and the test tube carrier 520. The test tube carrier 520 is able to be moved upwardly by the elastic force of the elastic member 560.

One end of the fluid transfer device 600 corresponds to the top of the test tube carrier 520, and another end of the fluid transfer device 600 corresponds to the test chip 100. In detail, each of the fluid transfer devices 600 includes a fluid driving member 610, a first flexible tube 620 and a second flexible tube 630.

In this embodiment, the first flexible tube 620 has an opening 621 and an opening 622 which are opposite to each other, and the second flexible tube 630 has an opening 631 and an opening 632 which are opposite to each other. The opening 621 of the first flexible tube 620 and the opening 631 of the second flexible tube 630 are connected to each other via the fluid driving member 610. The opening 622 of the first flexible tube 620 and the opening 632 of the second flexible tube 630 respectively correspond to the top of the test tube carrier 520 and the test chip 100. The fluid driving member 610 is used for driving the body fluid sample to flow from the first flexible tubes 620 to the second flexible tubes 630.

In this embodiment, the fluid driving member 610 is, for example, a syringe having a cylindrical tube (barrel) and a plunger. The body fluid sample L is able to be accommodated in the cylindrical tube. The plunger can be pulled and pushed along inside the cylindrical tube, allowing the syringe to draw and expel the body fluid sample L, but the present disclosure is not limited thereto. In other embodiments, the fluid driving member 610 can be a pump.

In this and some other embodiments, the body fluid test system 10 further includes a fixed carrier 650 and a movable holding member 660. The fixed carrier 650 is fixed to the base 510. The movable holding member 660 is movably disposed on the fixed carrier 650. In this embodiment, as show in FIG. 1, the movable holding member 660 is able to be moved in the direction of arrow D. The movable holding member 660 can be operated manually or by hydraulic oil pressure. Both of the two cylindrical tubes of the two aforementioned fluid driving members 610 are disposed on the fixed carrier 650. Both of the plungers of the two fluid driving members 610 are disposed on the movable holding member 660. Thus, by moving the movable holding member 660 upwardly, the plungers of the fluid driving members 610 can be pulled to draw the body fluid sample L contained in the test tubes 20. By moving the movable holding member 660 downwardly, the plungers of the fluid driving members 610 can be pushed to expel the body fluid sample L contained in the fluid driving members 610 to the test chip 100.

In this and some other embodiments, the body fluid test system 10 further includes two first clamping mechanisms 710 and a second clamping mechanism 720. The two first clamping mechanisms 710 are used for respectively clamping the two first flexible tubes 620 in order to prevent the body fluid sample L from flowing through the two first flexible tubes 620. The second clamping mechanism 720 is used for clamping the two second flexible tube 630 in order to prevent the body fluid sample L from flowing through the two second flexible tubes 630. In this embodiment, the first clamping mechanisms 710 and the second clamping mechanism 720 are used for controlling the flowing direction of the body fluid sample L, but the present disclosure is not limited thereto. In other embodiments, the flowing direction of the body fluid sample L can be controlled by a back pressure valve.

In this embodiment, the movable holding member 660, the first clamping mechanisms 710 and the second clamping mechanism 720 are operated electrically, but the present disclosure is not limited thereto. In other embodiments, the movable holding member 660, the first clamping mechanisms 710 and the second clamping mechanism 720 can be operated manually.

Please refer to FIG. 1, FIG. 4 and FIG. 5. FIG. 4 is a schematic plan view of the moving mechanism in FIG. 2 when a test tube carrier is located at a pre-testing position, and FIG. 5 is a schematic plan view of the moving mechanism in FIG. 2 when the test tube carrier is located at a testing position. In addition, for the purpose of description, the test tube carrier 520 is omitted in FIG. 4 and FIG. 5.

The method of operating the body fluid test system 10 includes at least two steps in general. In the first step, the body fluid sample L is left and untouched for a particular period of time until the body fluid sample is in a stable state. Then, in the second step, the body fluid sample L is tested.

In detail, in the first step, the test tube carrier 520 is, for example, pressed downwardly so that the second stop block 552 is able to press against the first stop block 551 and restrict the first stop block 551 from moving upwardly. Thus, the test tube carrier 520 is temporarily positioned at the pre-testing position (as shown in FIG. 4). Then, the test tubes 20 containing the body fluid samples L are disposed on the test tube carrier 520, one new test chip 100 and two new fluid transfer devices 600 are disposed on their intended positions, and the two openings 622 of the two first flexible tubes 620 are respectively put into two tube openings 22 of the two test tubes 20. Then, when the test tubes 20 is left and untouched for a particular period of time, the bubbles in the body fluid samples L are disappeared so that the body fluid samples L are in a stable state.

Then, in the second step, when the movable rod 571 is moved in the direction of arrow a (as shown in FIG. 5), the movable rod 571 bends the flexible arm 572 and forces the end of the flexible arm 572 connected to the movable rod 571 to move away from the first stop block 551, so the second stop block 552 is separated from the first stop block 551 and release the first stop block 551. Thus, by the decelerating assembly 540 and the elastic force of the elastic member 560, the test tube carrier 520 is lifted slowly from the pre-testing position (as shown in FIG. 4) to the testing position (as shown in FIG. 5) in the direction of arrow b. In such a case, the two openings 622 of the two first flexible tubes 620 respectively dive into the body fluid samples L contained in the two test tubes 20.

Before drawing the body fluid samples L contained in the two test tubes 20, the second clamping mechanism 720 clamps the two second flexible tubes 630. Thus, when the movable holding member 660 is moved upwardly, the plungers of the fluid driving members 610 respectively create negative pressure within the cylindrical tubes. Hence, the body fluid samples L contained in the two test tubes 20 are respectively drawn into the cylindrical tubes through the first flexible tubes 620. Then, the second clamping mechanism 720 is released, and the two first clamping mechanisms 710 respectively clamp the two first flexible tubes 620. In such a case, when the movable holding member 660 is moved downwardly, the body fluid samples L contained in the cylindrical tubes of the fluid driving members 610 are prevented from flowing back into the two test tubes 20 and only allowed to flow to the test chip 100 through the second flexible tubes 630.

Then, the light source 300 generates light incident on the body fluid samples L in the test chip 100, and the image capturing device 200 captures an image of the body fluid samples L for testing the body fluid samples L.

When the test is done, the used body fluid samples L are moved to the fluid processing device 400, the used test chip 100, the fluid transfer devices 600 and the test tubes 20 are detached and removed, and the test tube carrier 520 is pressed back to the pre-testing position for the next testing.

According to the moving mechanism and the body fluid test system having the moving mechanism as discussed above, since the test tube carrier of the moving mechanism can be moved upwardly relative to the base, the test tube containing the body fluid sample being left and untouched for a particular period of time is able to be moved from the pre-testing position to the testing position directly by the test tube carrier and still maintained in a stable state, thereby not affecting the diagnostic accuracy.

While this disclosure has been described in terms of several preferred embodiments, there are alterations, permutations, and equivalents, which fall within the scope of this disclosure. It should also be noted that there are many alternative ways of implementing the methods and apparatuses of the present disclosure. It is therefore intended that the following appended claims be interpreted as including all such alterations, permutations, and equivalents as fall within the true spirit and scope of the present disclosure.

What is claimed is:

1. A body fluid test system, comprising:
   a test chip;
   an image capturing device for capturing image of the test chip;
   a moving mechanism for test tube, comprising:
     a base; and
     a test tube carrier movably disposed on the base, and the test tube carrier being for carrying at least one test tube; and
   at least one fluid transfer device, one end of the fluid transfer device corresponding to the top of the test tube carrier, and another end of the fluid transfer device corresponding to the test chip;
   wherein the test tube carrier is movable upwardly from a pre-testing position to a testing position, when the test tube carrier is at the testing position, the fluid transfer device is for transferring a body fluid sample contained in the at least one test tube to the test chip.

2. The body fluid test system according to claim 1, wherein the moving mechanism further comprises a decelerating assembly, the decelerating assembly comprises a gear rack and a decelerating gear, the gear rack is disposed on one of the base and the test tube carrier, the decelerating gear is disposed on the other one of the base and the test tube carrier, and the decelerating gear is engaged to the gear rack.

3. The body fluid test system according to claim 1, wherein the moving mechanism further comprises a slide assembly, the slide assembly comprises a rail member and a slidable member, the rail member is disposed on the base, and the slidable member is disposed on the test tube carrier.

4. The body fluid test system according to claim 3, wherein the moving mechanism further comprises a stop assembly, the stop assembly comprises a first stop block and a second stop block, the first stop block is disposed on the slidable member, and the second stop block is movably disposed on the base so that the second stop block is press against the first stop block for restricting the movement of the first stop block or separated from the first stop block for releasing the first stop block.

5. The body fluid test system according to claim 1, wherein the moving mechanism further comprises an elastic member, two opposite ends of the elastic member are respectively connected to the base and the test tube carrier, and the elastic member is for moving the test tube carrier upwardly to the testing position.

6. The body fluid test system according to claim 1, wherein the at least one fluid transfer device comprises a fluid driving member, a first flexible tube and a second flexible tube, the first flexible tube has a first opening and a second opening, the second flexible tube has a third opening and a fourth opening, the first opening of the first flexible tube and the third opening of the second flexible tube are connected to each other via the fluid driving member, the second opening of the first flexible tube and the fourth opening of the second flexible tube respectively correspond to the top of the test tube carrier and the test chip, and the fluid driving member is for driving the body fluid sample to flow from the first flexible tube to the second flexible tube.

7. The body fluid test system according to claim 6, wherein the fluid driving member is a syringe.

8. The body fluid test system according to claim 6, further comprising at least one first clamping mechanism and a second clamping mechanism, the at least one first clamping mechanism being for clamping the first flexible tube and preventing the body fluid sample from flowing through the first flexible tube, and the second clamping mechanism being for clamping the second flexible tube and preventing the body fluid sample from flowing through the second flexible tube.

9. The body fluid test system according to claim 1, further comprising a light source for generating light incident on the test chip.

10. A moving mechanism for test tube, comprising:
a base;
a test tube carrier movably disposed on the base, and the test tube carrier being for carrying at least one test tube, wherein the test tube carrier is movable upwardly from a pre-testing position to a testing position;
a slide assembly, comprising a rail member and a slidable member, the rail member disposed on the base, and the slidable member disposed on the test tube carrier; and
a stop assembly, comprising a first stop block and a second stop block, the first stop block disposed on the slidable member, and the second stop block movably disposed on the base so that the second stop block is press against the first stop block for restricting the movement of the first stop block or separated from the first stop block for releasing the first stop block.

11. The moving mechanism according to claim 10, wherein the moving mechanism further comprises a decelerating assembly, the decelerating assembly comprises a gear rack and a decelerating gear, the gear rack is disposed on one of the base and the test tube carrier, the decelerating gear is disposed on the other one of the base and the test tube carrier, and the decelerating gear is engaged to the gear rack.

12. The moving mechanism according to claim 10, further comprising an elastic member, two opposite ends of the elastic member respectively connected to the base and the test tube carrier, and the elastic member being for moving the test tube carrier upwardly to the testing position.

* * * * *